United States Patent [19]

Sknottner-Lundin et al.

[11] Patent Number: 5,273,966
[45] Date of Patent: Dec. 28, 1993

[54] O-GLYCOSYLATED IGF-1

[75] Inventors: Anna Sknottner-Lundin, Ekerö; Linda Fryklund, Sollentuna; Par Gellerfors, Lidingö, all of Sweden

[73] Assignee: Kabi Pharmacia AB, Sweden

[21] Appl. No.: 654,611

[22] PCT Filed: Aug. 17, 1989

[86] PCT No.: PCT/EP89/00972
§ 371 Date: Apr. 22, 1991
§ 102(e) Date: Apr. 22, 1991

[87] PCT Pub. No.: WO90/02198
PCT Pub. Date: Mar. 8, 1990

[30] Foreign Application Priority Data

Aug. 20, 1988 [GB] United Kingdom ............... 8819826

[51] Int. Cl.⁵ ............... A61K 37/36; C12P 21/00; C12P 21/02; C07K 7/40
[52] U.S. Cl. ............... 514/12; 514/3; 514/4; 514/8; 530/399; 530/324; 530/303; 435/172.3; 435/172.2; 435/69.4
[58] Field of Search ............... 514/3, 8; 530/303, 304, 530/324, 399; 435/69, 70

[56] References Cited

PUBLICATIONS

Ratner, *Biotechnology*, vol. 7, No. 11, Nature Publishing, 1129–1133, Nov. 1989.
Hard et al., FEBS Letters, 248, No. 1,2, 111–114, May 1989.
Sknottner et al., Acta Palediatrica Scandinavia (Suppl.), 325, 107–111, 1986.

*Primary Examiner*—F. T. Moezie
*Attorney, Agent, or Firm*—Pollock, Vande Sande & Priddy

[57] ABSTRACT

The present invention provides an O-Glycosylated Insulin-like Growth Factor 1 (IGF-1) analog of Insulin-like Growth Factor 1, a seventy amino acids single polypeptide chain which displays relatively high homology with proinsulin, essentially free from unglycosylated IGF-1.

3 Claims, 7 Drawing Sheets

Fig.2.

Yeast alpha-mating factor leader peptide - IGF-1 met-arg-phe-pro-ser-ile-phe-thr-ala-val-leu-phe-ala-ala-ser-ser-
1                                      10 ala-leu-ala-ala-pro-val-asn-thr-thr-thr-glu-asp-glu-thr-ala-gln-ile-
           20                                      30 pro-ala-glu-ala-val-ile-gly-tyr-ser-asp-leu-glu-gly-asp-phe-asp-
                        40 val-ala-val-leu-pro-phe-ser-asn-ser-thr-asn-asn-gly-leu-leu-phe-
50                                      60 ile-asn-thr-thr-ile-ala-ser-ile-ala-ala-lys-glu-glu-gly-val-ser-leu-
              70                                    80 asp-lys-arg-|-gly-pro-glu-_thr_-leu-cys-gly-ala-glu-leu-val-asp-ala-
         ↳ IGF-1           90 leu-gln-phe-val-cys-gly-asp-arg-gly-phe-tyr-phe-asn-lys-pro-_thr_-
100                                     110 gly-tyr-gly-_ser-ser-ser_-arg-arg-ala-pro-gln-_thr_-gly-ile-val-asp-
              120                                   130 glu-cys-cys-phe-arg-_ser_-cys-asp-leu-arg-arg-leu-glu-met-tyr-
                              140 cys-ala-pro-leu-lys-pro-ala-lys-_ser_-ala
150                       155

Potential O-linked glycosylation sites are underlined

Tryptic map of glycosylated and non glycosylated IGF-1

Structure of the two mannose residues bound to Thr$_{29}$ in yeast derived human IGF-1

αMan(1→2)αMan 1→Thr$_{29}$

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 155 amino acids
    ( B ) TYPE: amino acid
    ( D ) TOPOLOGY: linear ( i i ) MOLECULE TYPE: protein ( i x ) FEATURE:
    ( A ) NAME/KEY: Protein
    ( B ) LOCATION: 1..85
    ( D ) OTHER INFORMATION: /note="alpha-mating factor leader peptide"

( i x ) FEATURE:
    ( A ) NAME/KEY: Protein
    ( B ) LOCATION: 86..155
    ( D ) OTHER INFORMATION: /label=IGF-1

( i x ) FEATURE:
    ( A ) NAME/KEY: Protein
    ( B ) LOCATION: 1..155
    ( D ) OTHER INFORMATION: /note="alpha-mating factor leader peptide-IGF-1 hybrid protein"

( i x ) FEATURE:
    ( A ) NAME/KEY: Binding-site
    ( B ) LOCATION: 89
    ( D ) OTHER INFORMATION: /note="potential glycosylation site"

( i x ) FEATURE:
    ( A ) NAME/KEY: Binding-site
    ( B ) LOCATION: 114
    ( D ) OTHER INFORMATION: /note="potential glycosylation site"

( i x ) FEATURE:
    ( A ) NAME/KEY: Binding-site
    ( B ) LOCATION: one-of(118, 119, 120)
    ( D ) OTHER INFORMATION: /note="potential glycosylation site"

( i x ) FEATURE:
    ( A ) NAME/KEY: Binding-site
    ( B ) LOCATION: 126
    ( D ) OTHER INFORMATION: /note="potential glycosylation site"

( i x ) FEATURE:
    ( A ) NAME/KEY: Binding-site
    ( B ) LOCATION: 136
    ( D ) OTHER INFORMATION: /note="potential glycosylation site"

( i x ) FEATURE:

(A) NAME/KEY: Binding-site
(B) LOCATION: 154
(D) OTHER INFORMATION: /note="potential glycosylation site"

(xi) SEQUENCE DESCRIPTION: SEQ ID NO:1:

```
Met Arg Phe Pro Ser Ile Phe Thr Ala Val Leu Phe Ala Ala Ser Ser
1               5                   10                  15
Ala Leu Ala Ala Pro Val Asn Thr Thr Glu Asp Glu Thr Ala Gln
            20              25                  30
Ile Pro Ala Glu Ala Val Ile Gly Tyr Ser Asp Leu Glu Gly Asp Phe
        35              40                  45
Asp Val Ala Val Leu Pro Phe Ser Asn Ser Thr Asn Asn Gly Leu Leu
    50              55                  60
Phe Ile Asn Thr Thr Ile Ala Ser Ile Ala Ala Lys Glu Glu Gly Val
65              70                  75                          80
Ser Leu Asp Lys Arg Gly Pro Glu Thr Leu Cys Gly Ala Glu Leu Val
                85              90                  95
Asp Ala Leu Gln Phe Val Cys Gly Asp Arg Gly Phe Thr Phe Asn Lys
            100             105                 110
Pro Thr Gly Tyr Gly Ser Ser Ser Arg Arg Ala Pro Gln Thr Gly Ile
        115             120                 125
Val Asp Glu Cys Cys Phe Arg Ser Cys Asp Leu Arg Arg Leu Glu Met
    130             135                 140
Tyr Cys Ala Pro Leu Lys Pro Ala Lys Ser Ala
145             150             155
```

(2) INFORMATION FOR SEQ ID NO:2:

(i) SEQUENCE CHARACTERISTICS:
        (A) LENGTH: 70 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..70
        (D) OTHER INFORMATION: /label=IGF-1

(ix) FEATURE:
        (A) NAME/KEY: Binding-site
        (B) LOCATION: 4
        (D) OTHER INFORMATION: /note="potential glycosylation site"

(ix) FEATURE:
        (A) NAME/KEY: Binding-site
        (B) LOCATION: 29
        (D) OTHER INFORMATION: /note="potential glycosylation site"

(ix) FEATURE:
        (A) NAME/KEY: Binding-site
        (B) LOCATION: one-of(33, 34, 35)
        (D) OTHER INFORMATION: /note="potential glycosylation sites"

(ix) FEATURE:
        (A) NAME/KEY: Binding-site
        (B) LOCATION: 41
        (D) OTHER INFORMATION: /note="potential glycosylation site"

(ix) FEATURE:
        (A) NAME/KEY: Binding-site
        (B) LOCATION: 51
        (D) OTHER INFORMATION: /note="potential glycosylation site"

( i x ) FEATURE:
    ( A ) NAME/KEY: Binding-site
    ( B ) LOCATION: 69
    ( D ) OTHER INFORMATION: /note="potential glycosylation site"

( i x ) FEATURE:
    ( A ) NAME/KEY: Cleavage-site
    ( B ) LOCATION: (21 22)
    ( D ) OTHER INFORMATION: /note="trypsin cleavage site"

( i x ) FEATURE:
    ( A ) NAME/KEY: Cleavage-site
    ( B ) LOCATION: (24 25)
    ( D ) OTHER INFORMATION: /note="trypsin cleavage site"

( i x ) FEATURE:
    ( A ) NAME/KEY: Cleavage-site
    ( B ) LOCATION: (29 30)
    ( D ) OTHER INFORMATION: /note="trypsin cleavage site"

( i x ) FEATURE:
    ( A ) NAME/KEY: Cleavage-site
    ( B ) LOCATION: (31 32)
    ( D ) OTHER INFORMATION: /note="trypsin cleavage site"

( i x ) FEATURE:
    ( A ) NAME/KEY: Cleavage-site
    ( B ) LOCATION: (36 37)
    ( D ) OTHER INFORMATION: /note="trypsin cleavage site"

( i x ) FEATURE:
    ( A ) NAME/KEY: Cleavage-site
    ( B ) LOCATION: (37 38)
    ( D ) OTHER INFORMATION: /note="trypsin cleavage site"

( i x ) FEATURE:
    ( A ) NAME/KEY: Cleavage-site
    ( B ) LOCATION: (41 42)
    ( D ) OTHER INFORMATION: /note="trypsin cleavage site"

( i x ) FEATURE:
    ( A ) NAME/KEY: Cleavage-site
    ( B ) LOCATION: (50 51)
    ( D ) OTHER INFORMATION: /note="trypsin cleavage site"

( i x ) FEATURE:
    ( A ) NAME/KEY: Cleavage-site
    ( B ) LOCATION: (55 56)
    ( D ) OTHER INFORMATION: /note="trypsin cleavage site"

( i x ) FEATURE:
    ( A ) NAME/KEY: Cleavage-site
    ( B ) LOCATION: (56 57)
    ( D ) OTHER INFORMATION: /note="trypsin cleavage site"

( i x ) FEATURE:
    ( A ) NAME/KEY: Cleavage-site
    ( B ) LOCATION: (60 61)
    ( D ) OTHER INFORMATION: /note="trypsin cleavage site"

( i x ) FEATURE:
    ( A ) NAME/KEY: Cleavage-site
    ( B ) LOCATION: (68 69)
    ( D ) OTHER INFORMATION: /note="trypsin cleavage site"

( i x ) FEATURE:
    ( A ) NAME/KEY: Cross-links
    ( B ) LOCATION: 6..48

( i x ) FEATURE:
    ( A ) NAME/KEY: Cross-links
    ( B ) LOCATION: 18..61

( i x ) FEATURE:
    ( A ) NAME/KEY: Cross-links
    ( B ) LOCATION: 47..52

( x i ) SEQUENCE DESCRIPTION: SEQ ID NO:2:

```
Gly Pro Glu Thr Leu Cys Gly Ala Glu Leu Val Asp Ala Leu Gln Phe
 1               5                  10                  15
```

```
Val Cys Gly Asp Arg Gly Phe Thr Phe Asn Lys Pro Thr Gly Tyr Gly
            20                  25              30

Ser Ser Ser Arg Arg Ala Pro Gln Thr Gly Ile Val Asp Glu Cys Cys
        35              40                  45

Phe Arg Ser Cys Asp Leu Arg Arg Leu Glu Met Tyr Cys Ala Pro Leu
    50                  55              60

Lys Pro Ala Lys Ser Ala
65                  70
```

O-GLYCOSYLATED IGF-1

FIELD OF THE INVENTION

The present invention relates to glycosylated insulin-like growth factor-1.

BACKGROUND OF THE INVENTION

Insuliln-like growth factor (IGF-1) is a 70 amino acid single polypeptide chain factor which displays relatively-high homology with proinsulin. IGF-1 is known to have a mediating effect on the action of growth hormone and also to display insulin-like properties. When produced in nature by the human body, IGF-1 is unglycosylated.

IGF-1 has potential uses as a pharmaceutical agent both in the treatment of pituitary dwarfism and also diabetes. In the latter case it would be useful either as a replacement for insulin or as an adjunct to insulin. Although insulin is the traditional treatment for diabetes, type-2 diabetics have developed a resistance to insulin which means that even if very high doses of insulin are administered, the patients can still suffer from hyperglycemia. Further, excessive doses of insulin can lead to undesirable side effects such as kidney complaints, obesity, and a disturbed water balance.

Although unglycosylated IGF-1 could be used as a replacement or adjunct for insulin in an attempt to overcome some of these problems, a high proportion of unglycosylated IGF-1 tends to be sequestrated by specific binding proteins circulating in the bloodstream. Therefore, relatively high doses of the IGF-1 need to be administered for the desired pharmaceutical effect to be attained.

We have now discovered that expression of IGF-1 in yeast cells results in the production, along with the normal unglycosylated form, of an O-glycosylated analog of IGF-1, for example, an analog which carries two mannose residues on the Thr $_{29}$ amino acid of the polypeptide chain. Tests have shown that O-glycosylated IGF-1 has a reduced affinity for the binding proteins and that a desired reduction in blood sugar level can be achieved by a reduced dose of O-glycosylated IGF-1 as compared with the normal unglycosylated protein. This observed affinity for the binding protein will have a profound effect on the profile and dose dependency. The other effects, although not so pronounced are of importance in the total clinical effect.

The expression "O-glycosylated IGF-1" embraces O-glycosylated molecules which comprise fragments of the whole IGF-1 polypeptide sequence, provided that those fragments display qualitatively the growth-hormone mediating effect and/or insulin-like properties of IGF-1.

SUMMARY OF THE INVENTION

According to one aspect of the invention, we therefore provide O-glycosylated IGF-1 essentially free from unglycosylated IGF-1.

According to another aspect of the invention we provide O-glycosylated IGF-1 in which the glycosylation is at the Thr $_{29}$ amino acid of the polypeptide chain.

According to yet another aspect of the invention, we provide O-glycosylated IGF-1 in which the glycosylation comprises two or more mannose residues attached to the same threonine residue of the IGF-1 polypeptide chain.

According to a further aspect of the invention, we provide an O-glycosylated analog of IGF-1 in which two or more mannose residues are attached to the Thr $_{29}$ amino acid of the polypeptide chain.

According to a still further aspect of the invention, we provide a method of obtaining O-glycosylated IGF-1 by the expression of IGF-1 in yeast cells, and isolating O-glycosylated IGF-1 from the medium. Preferably, the yeast is Saccharomyces cerevisiae.

The gene for IGF-1 is preferably linked to DNA coding for a secretory signal sequence, for example that of the gene for α-mating factor, so that mature authentic IGF-1 which has been O-glycosylated is secreted from the cytoplasm of the yeast cells. The α-mating factor is a 13-amino acid peptide secreted by yeast cells of the α-mating type to promote efficient conjugation of a cells to form a α-diploid cells. Sequence data of the α-mating factor structural gene shows that the α-mating factor is initially synthesized as a 165 amino acid precursor containing an 85 amino acid leader peptide and four coding regions each interrupted by an 8 amino acid spacer peptide. The 85 amino acid leader polypeptide contain a 19 amino acid signal sequence involved in targeting the precursor to the endoplasmatic membrane.

We further provide a pharmaceutical composition containing O-glycosylated IGF-1 but substantially no unglycosylated IGF-1, and a pharmaceutically-acceptable carrier, diluent, or excipient. The composition may also include insulin.

According to another feature of the invention, we provide a method of preparing a pharmaceutical composition comprising mixing O-glycosylated IGF-1 and unglycosylated IGF-1. The plasmid utilised for the expression of IGF-1 in yeast may be p539/12, the construction of which is described in the following Example. Other yeast expression plasmids would also be suitable.

BRIEF DESCRIPTION OF THE DRAWINGS

By way of example only, a process for the construction of a plasmid carrying the gene for IGF-1, transformation of Saccharomyces cerevisiae with that plasmid, and expression of mature human O-glycosylated IGF-1 from the transformed yeast cells will now be described in detail, with reference to the accompanying figures, in which:

FIG. 1a is a restriction map of plasmid p539/12;

VARIOUS AND PREFERRED EMBODIMENTS OF THE INVENTION

EXAMPLE

The IGF-1 gene was expressed in *Saccharomyces cerevisiae*, using an α-mating factor leader peptide-IGF-1 expression plasmid, p539/12.

Plasmid and yeast mutant strain

Figure 1:
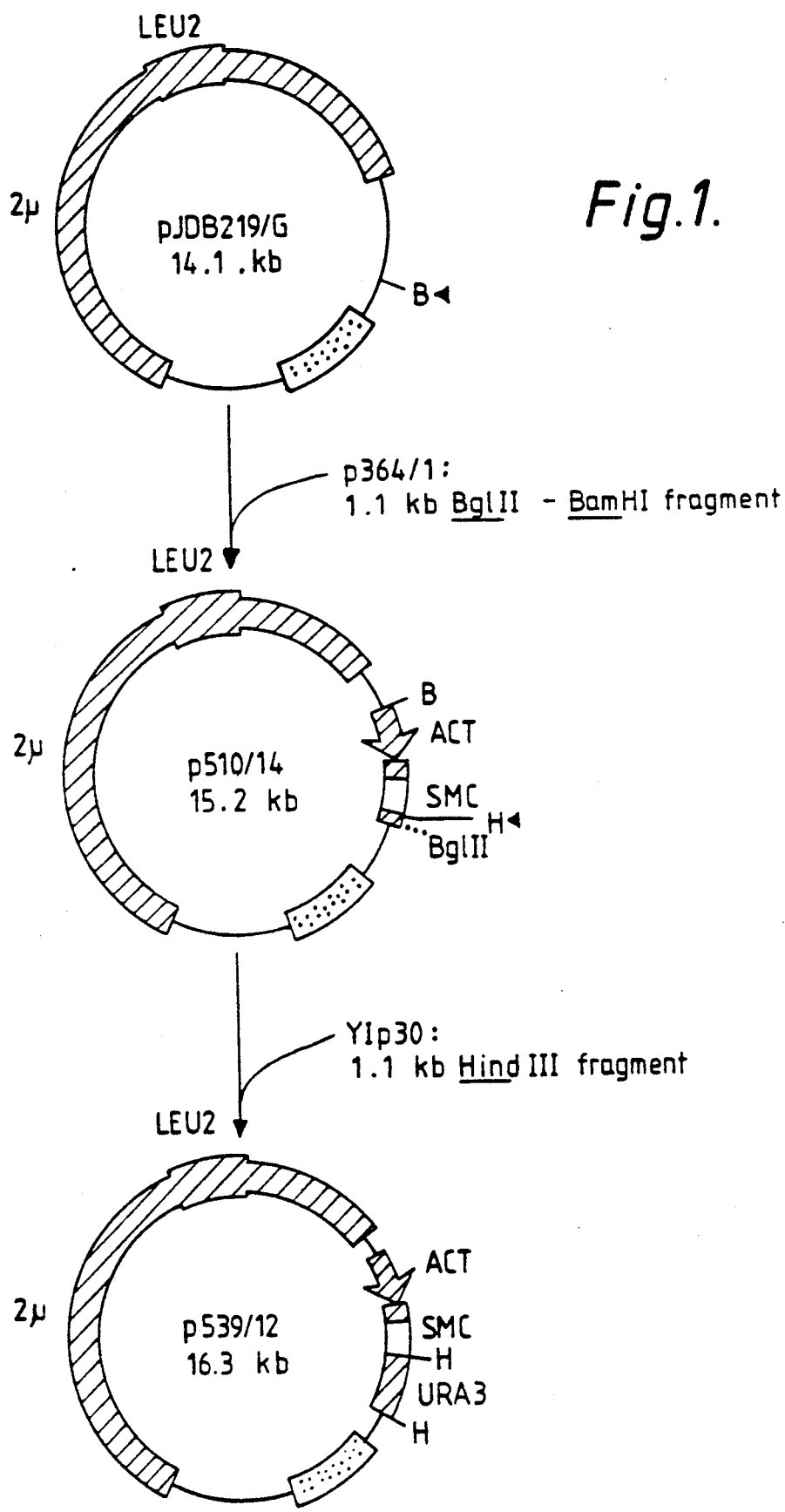
FIG. 1 illustrates the construction of IGF-1 expression plasmid p539/12.

Plasmid p539/12 was constructed by Dr. J. F. Ernst at Biogen S.A. Ch-1227, Geneva, Switzerland. Its construction is as follows. Plasmid pJDB219/G was constructed from JDB219 (Beggs, J. D., In: A. Benzon Symposium 16, editors: D. von Wettstein, J. Fries, M. Kielland-Brand & A. Stenderup, Munksgaard, Copenhagen, 383–389, 1981) by inserting a 1.7 kb SalI fragment carrying the APH gene Tn903 (Ern st, J. F. and R. C. Chan. *J. Bacteriol.* 163, 8–14, 1985) into the single SalI site of JDB219 (stripped box in FIG. 1). The SMC expression unit from plasmid p364/1, encompassing the ACT promoter, the MF α 1 leader sequence and the SMC gene were transferred as a 1.1 kb BglII-BamHI fragment into the single BamHI site of pJDB219/G. The resulting plasmid, p510/14, was linearized by partial digestion with HindIII and a 1.1 kb HindIII fragment carrying the yeast URA3 gene, which was derived from YIp30 (Botstein, D. et al., Gene 8, 17–24, 1979) was inserted into p510/14 to create p539/12 which carries the markers $Kan^R G418^R Ura3 + Leu2 +$. An outline of its genetic elements are shown in FIG. 1a. The production of IGF-1 was carried out in the *Saccharomyces cerevisiae* mutant strain YE 449 (Mat α leu 2, ura 3-52, prbl-1122, pep 4-3, cir 4 °).

Figure 2:
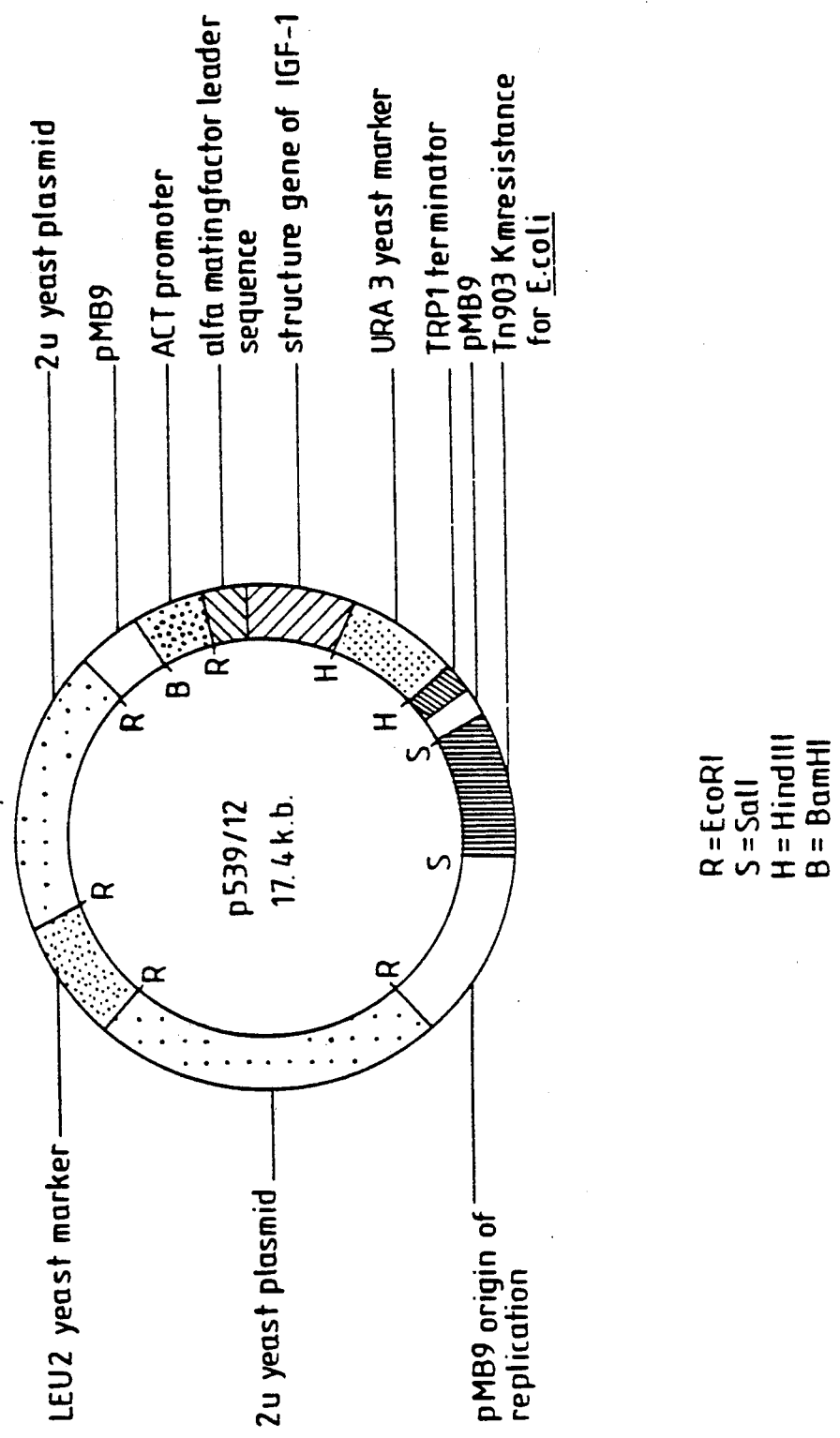
FIG. 2 shows the polypeptide structure SEQ ID:1 of the fusion between the α-mating factor leader sequence and IGF-1.
Figure 3:
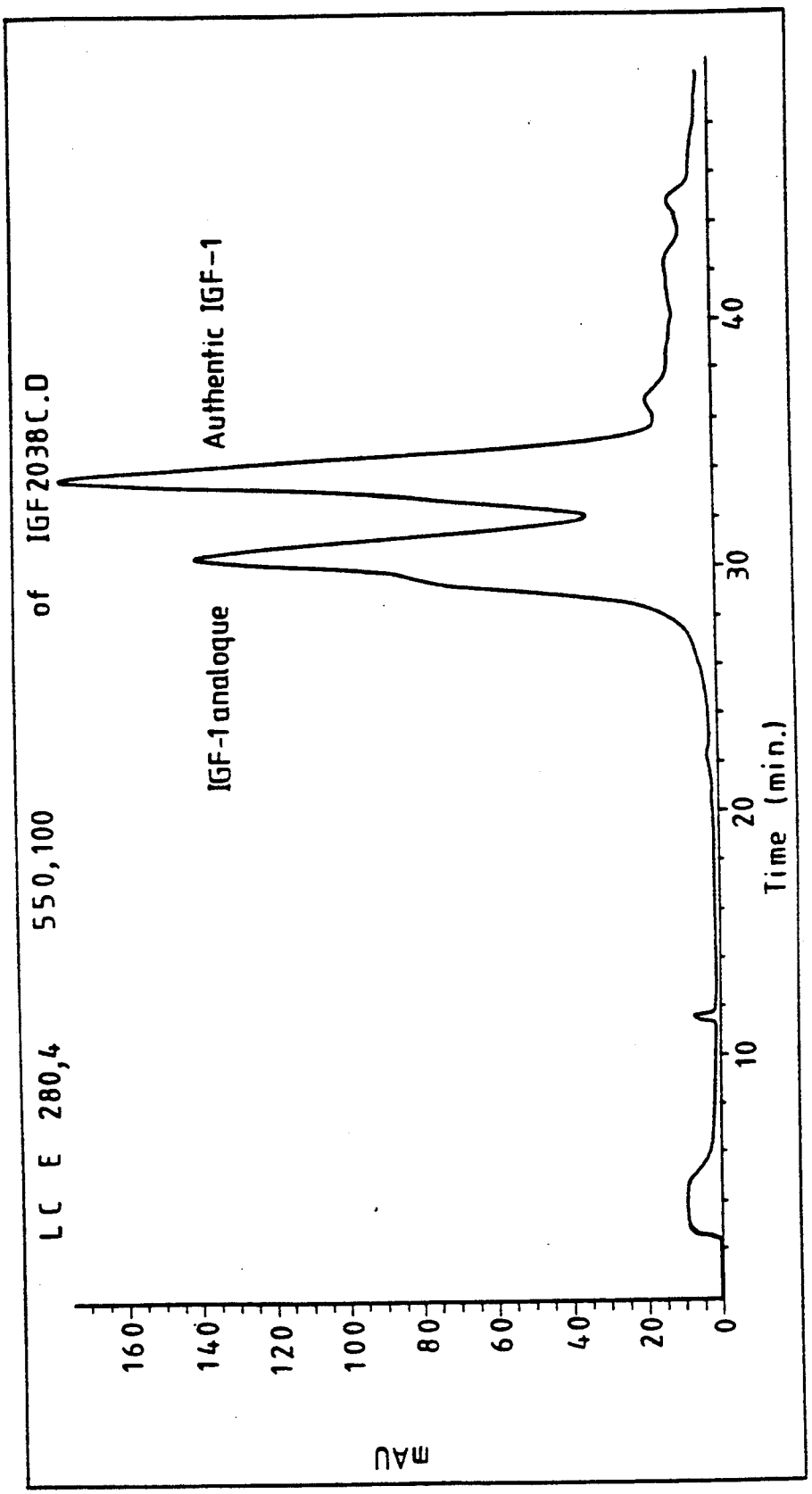
FIG. 3 shows the separation of the two forms of IGF-2 by HI-HPLC.

The plasmid is an improved version of other IGF-1 expression plasmids, reported earlier (Ernst J. F. (1986) DNA 5, 483–491). The total amino acid sequence SEQ ID:1 (155 amino acids) for the α-mating factor leader peptide-IGF-1 hybrid protein is shown in FIG. 2. The α-mating factor leader peptide comprises the first 85 residues and IGF-1 the remaining 70 residues. Several possible O-linked glycosylation sites are present in the IGF-1 sequence. These are indicated. The newly synthesized 155 amino acid long α-mating factor leader peptide-IGF-1 hybrid protein was secreted out from the cell into the medium. During this process the hybrid protein was cleaved by an endogenous yeast peptidase (KEX2), generating the authentic IGF-1 molecule with its correct N-terminal amino acid (Gly). However, in addition to the authentic form of human IGF-1 a new analog of human IGF-1 was also synthesized and secreted. The yeast fermentation medium contained approximately 50% of authentic human IGF-1 and 50% of the analog. These two IGF-1 forms were isolated from the medium using traditional biochemical separation techniques. The final separation of the IGF-1 analog from authentic human IGF-1, was achieved by hydrophobic interaction chromatography (HI-HPLC) using a TSK-Phenyl-5PW matrix (FIG. 3). The IGF-1 analog eluted earlier than authentic IGF-1, indicating that it is slightly more hydrophilic.

It was found by sodium dodecylsulfate polyacrylamide gel electrophoresis (SDS-PAGE) that authentic IGF-1 had a slightly lower molecular weight than the analog and the higher molecular weight (approx. 400 daltons) exhibited by the analog suggests that this form has molecules bound to the polypeptides chain, most likely carbohydrates added during the secretion process.

The amino acid composition of the IGF-1 analog was determined and found to be identical to that of the authentic molecule. Hence, the slightly more hydrophilic property of the IGF-1 analog, as deduced from the HI-HPLC experiment, is not due to a change in the polypeptide backbone, but rather some other structural modification. Yeast cells are known to contain glycoproteins, and the possibility that the new analog was a glycosylated form of IGF-1 was investigated.

ConA has been widely used in the study of glycoproteins due to its high affinity for oligosaccharide chains containing three or more mannose residues. Its carbohydrate specificity has been determined (α-D-Man > α-D-Glc > α-DGlcNAc).

Figure 4:
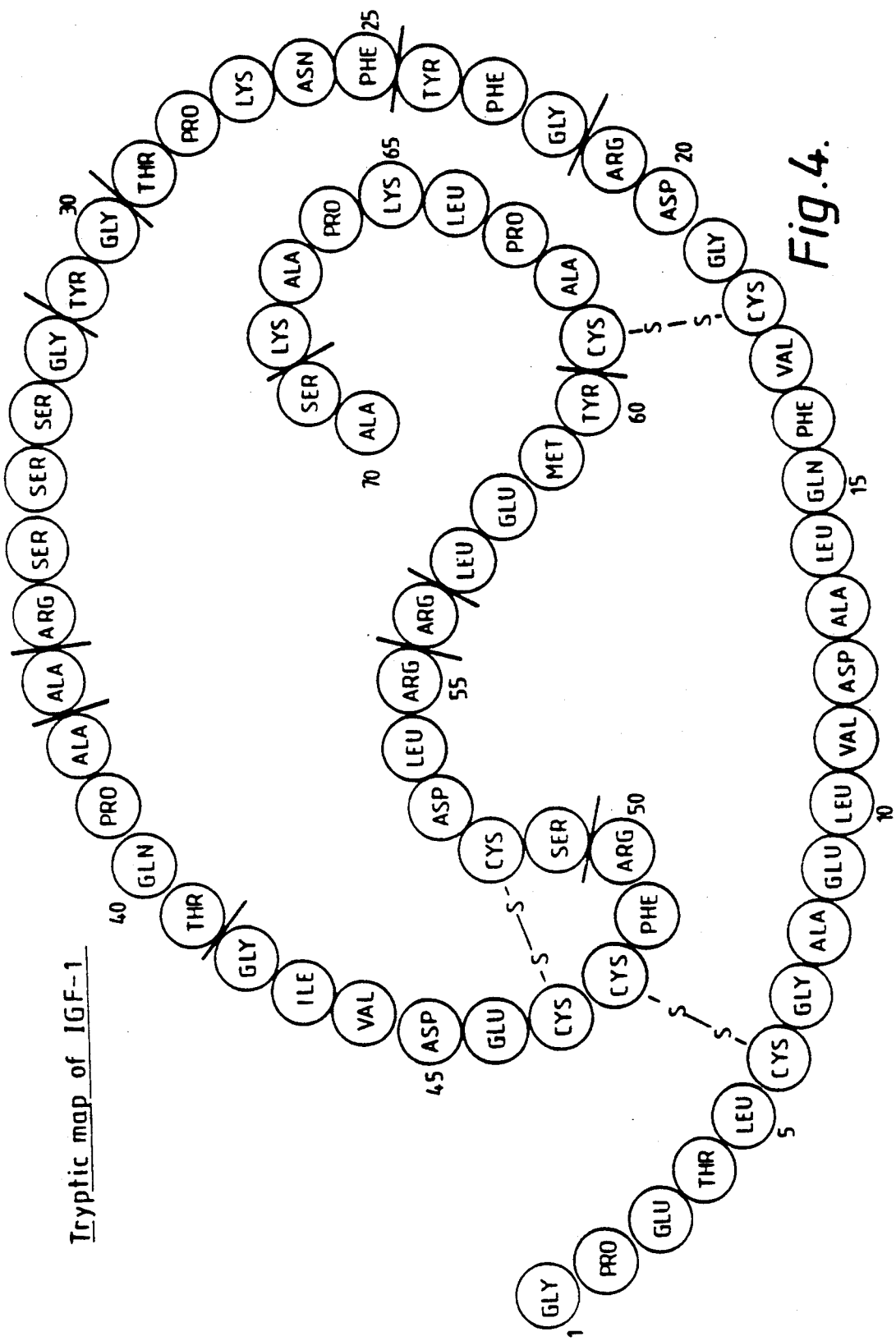
FIG. 4 shows the structure of IGF-1 with the tryptic fragments separated by transverse lines.

ConA blotting was carried out after sodium dodecylsulphate polyacrylamide gel electrophoresis (SDS-PAGE) of the IGF-1 analog and authentic human IGF-1 (FIG. 4). ConA binding was observed to the IGF-1 analog but not to the authentic form, indicating that the analog is a glycoprotein.

The carbohydrate moiety bound to the IGF-1 polypeptide background was identified by gas chromatography mass-spectrometry (GC/MC) after alkali hydrolysis (4M TFA, 120° C., 15') and subsequent reduction (NaBH) and acetylation. A peak (7.7 minutes) was found after gas chromatography when the IGF-1 analog was analyzed. No such peak was observed when authentic IGF-1 was analyzed (not shown). The material eluting at 7.7 minutes was further subjected to mass-spectrometry analysis. A mass-spectrum identical to a mannose reference mass-spectrum, was found demonstrating unambiguously that the IGF-1 analog contains mannose. Quantitation of the mannose content by gas chromatography against a calibrated mannose standard showed that the mannose content was approximately 2.1% (w/w). No mannose or other carbohydrates were found in the authentic IGF-1 form.

TRYPTIC MAP ANALYSIS

GlcNAc (N-acetyl glucosamine) has been shown always to be the first carbohydrate residue in N-linked glycosylation. Since no GlcNAc was found in the IGF-1 analog, the glycosylation has to be of the O-linked type, which can occur only to serine or threonine residues. IGF-1 contains 5 serine residues (Ser $_{33}$; Ser $_{34}$; Ser $_{51}$, and Ser $_{69}$), and 3 threonine residues (Thr $_4$, Thr $_{29}$; and Thr $_{41}$). (See FIG. 2).

To identify the glycosylated serine or threonine residue(s), the IGH-1 analog was digested with trypsin (the polypeptide chain cleaves after Arg and Lys residues) to generate shorter tryptic fragments. These were subsequently separated by RP-HPLC and their mobility compared to their corresponding counterparts generated by trypsin digestion of authentic IGF-1. Any change in mobility relative to the standard (authentic IGF-1) would reveal the glycosylated tryptic fragment.

Figure 5:
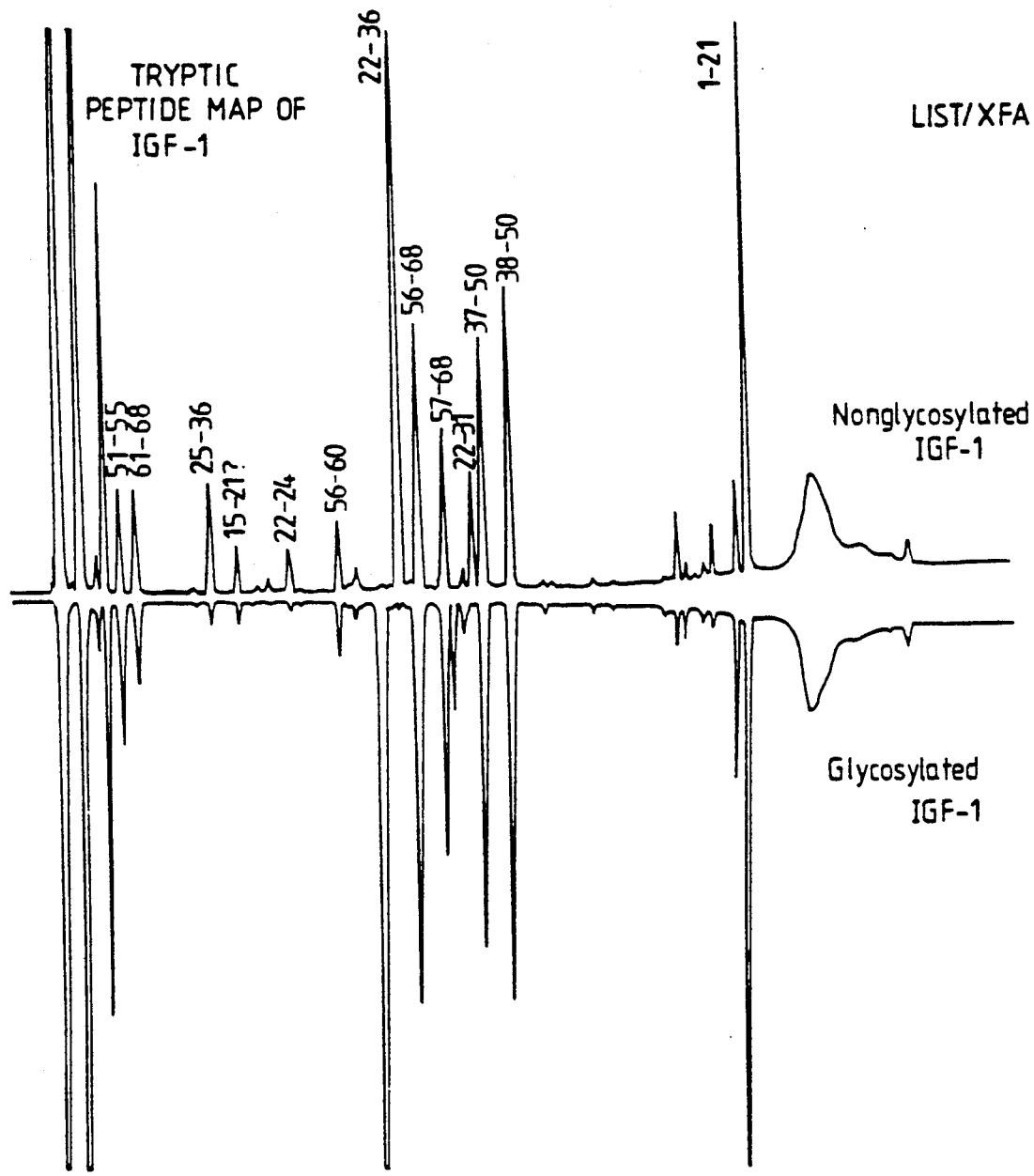
FIG. 5 is a tryptic map showing both forms of IGF-1.
Figure 6:
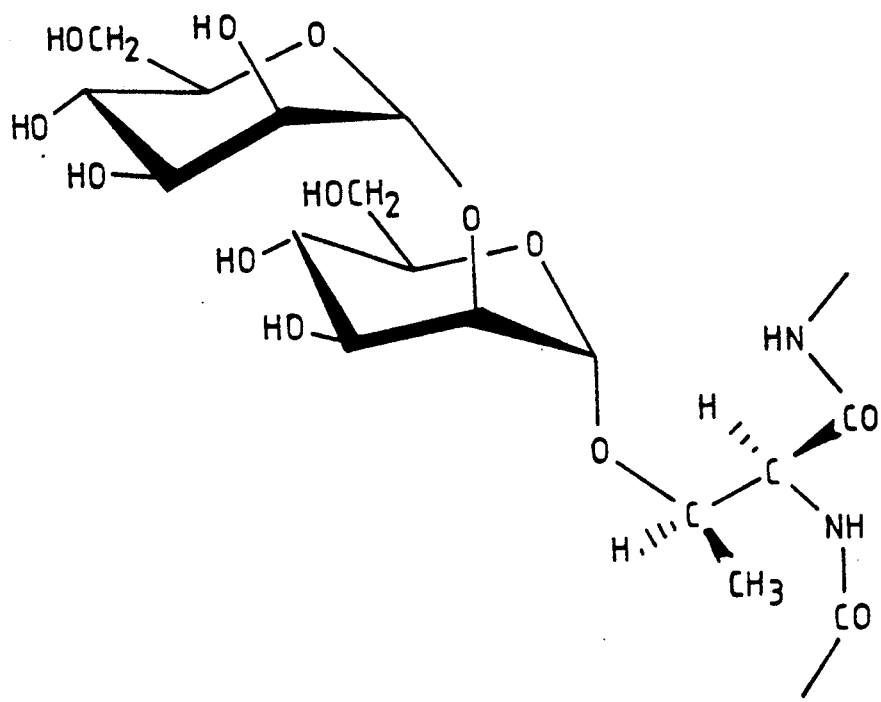
FIG. 6 shows the structure SEQ ID:2 of the two mannose residues bound to Thr $_{29}$ in the O-glycosylated form of IGF-1.

FIG. 4 shows the tryptic map of authentic IGF-1 SEQ ID:2. Thirteen unique fragments were separated, the different fragments being shown separated by transverse lines. The identity of these fragments were determined by amino acid analysis. These fragments fit with the seven tryptic cleavage points (Arg, Lys) in IGF-1 plus the three chymotryptic-like cleavages that have also taken place. When the tryptic map of IGF-1 analog was compared to authentic human IGF-1 a slight difference in elution time for tryptic fragments 22–36 was observed (FIG. 5). No other difference could be detected. The analysis shows clearly that the mannosylation site is within tryptic fragments 22-36. Based on its sequence, (-Gly-Phe-Tyr-Phe-Asn-Lys-Pro-Thr-Gly-Tyr-Ser-Ser-Ser-Arg-) four possible O-linked glycosylation sites are present, e.g. Thr $_{29}$; Ser $_{33}$; Ser $_{34}$; Ser $_{35}$.

The tryptic fragment 22-36 was isolated from the IGF-1 analog as well as from authentic IGF-1. These fragments were analyzed by protein sequence analysis. Thr present in the tryptic fragments from the IGF-1 analog was the only amino acid that migrated anomalously, demonstrating that it had been modified. No other differences in the entire sequence 22-36 were found between the two tryptic fragments. No modification was observed in the three consecutive serine residues Ser $_{33}$; Ser $_{34}$; or Ser $_{35}$; showing that these had not been glycosylated. Hence, these results demonstrate unambiguously that Thr $_{29}$ in the IGF-1 analog is the only amino acid which binds mannose. No other serine or threonine has been O-glycosylated.

To determine accurately the number of mannose residues bound to Thr $_{29}$, the tryptic fragment 22-36 isolated from the IGF-1 analog was analyzed by mass-spectrometry. This showed a molecular weight difference between the mannosylated and the non-mannosylated fragment of 324. Assuming a molecular weight for peptide bound mannose of 162 a stoichiometry of 2 mannose residues per tryptic fragment can be calculated. Consequently, each IGF-1 molecule contains two mannose residues bound to Thr $_{29}$. The structure of the two mannose residues bound to Thr $_{29}$ in the IGF-1 analog molecule was determined by H-NMR spectroscopy and is shown in FIG. 15.

BIOLOGICAL ACTIVITY

It was clearly shown after incubation with radiolabelled forms of IGF-1 that the O-glycosylated IGF-1 bound less well to the high molecular weight binding protein (150K) in both normal human serum and normal rat serum but no difference in the serum profiles was obtained when the serum from hypophysectomized rats was used. The area under the curves of the high and low molecular weight peaks indicated that only between 50 and 60% of the O-glycosylated IGF-1 was bound to the large molecular weight form compared to the authentic IGF-1. A small increase in binding to the low molecular weight form was observed, but the increase was not large enough to account for the change in ratio between binding to the high and low carriers, respectively.

In freshly prepared rat hepatocytes the two forms of IGF-1 had a dose-dependent effect on the transport into the cells of the non-metabolizable amino acid ($\alpha$-AIB). The results indicate that the glycosylated form was slightly more effective at the high concentration used (1 mole/l) than was the authentic IGF-1. The results on gluconeogenesis in hepatocytes after incubation with either of the IGF-1s or insulin showed that no effect was observed when insulin or authentic IGF-1 were added, which is what would be expected. However, by addition of the O-glycosylated IGF-1 an unexpected increase in the amount of glucose found in the medium was observed. This effect seems to be due to the mannose bound to the IGF-1 since the addition of the equivalent concentration of mannose alone resulted in the same effect. The effects were slightly lower than that observed with glucagon. An acute insulin-like activity measured as the hypoglycemia induced in hypophysectomized rats, could be demonstrated for both O-glycosylated and authentic IGF-1. A dose of 10 ug/rat, induced a pronounced hypoglycemia with both peptides. The nadir was observed at 30-45 minutes and the glucose levels had returned to initial after approximately 2 hours. The effect of the O-glycosylated IGF-1 was slightly greater than that of the authentic IGF-1 at similar doses, the maximal decrease in blood glucose being −27% at 45 min. for the O-glycosylated form, compared to −14.4% at 30 minutes for authentic IGF-1.

The results of the in vivo membrane transport showed that the maximal effect was reached after approximately 2 hours, where a plateau was observed. No significant difference between the peptides was observed, although there was a tendency for the O-glycosylated IGF-1 to be slightly more effective.

Preliminary calculations of the half-lives (T $_{\frac{1}{2}}$) of the O-glycosylated (mannosylated) and authentic IGF-1 were done. This resulted in T $_{\frac{1}{2}}$ of the $\alpha$-phase of 3 minutes and 4 minutes, respectively, in normal rats, whereas the half-lives of the $\alpha$-phase in hypophysectomized rats were slightly longer, i.e. 8 and 11 minutes for O-glycosylated and authentic IGF-1, respectively. The half-lives of the $\alpha$-phases, however, were in normal rats 3.5 hours and 5.3 hours, respectively, and in hypophysectomized rats 3.3 hours and 3.5 hours, respectively.

In summary, the O-glycosylated IGF-1 has been compared to the authentic IGF-1 in several different biological assays in vitro and in vivo. No significant difference in their specific activity according to placental receptor assay or radioimmunosassay was observed indicating that the mannosylated amino acid is not involved in the binding to either the IGF-1 receptor or to the site binding to the antibody.

This is also evident from the experiment showing different effects in vitro. Both IGF-1 forms have shown similar effects on membrane transport (amino acids) in hepatocytes. If binding to these receptors had been disturbed, a difference between the two forms would have been observed.

One unexpected finding, however, was observed in vitro in the hepatocytes, namely the fact that O-glycosylated IGF-1 increased the amount of glucose in the medium. This effect was also found by the addition of only mannose. It is well known that mannose can enter the gluconeogenetic pathway at the step of fructose-6-phosphate after conversion by phosphomannoisomerase. The slightly increased activity of O-glycosylated IGF-1 on the membrane transport, might be explained by the possibility that the cells use the mannose for generating energy.

It was recently demonstrated that the receptor for a peptide homologue insulin-like growth factor II (IGF-II) was apparently equivalent to the mannose-6-phosphate receptor, which is involved in lysosomal targeting. It has further been shown that addition of mannose-6-phosphate increased binding of IGF-II to its receptor two-fold, indicating that modulation of the receptor might occur.

The difference in binding to the high molecular weight binding protein between the two forms of IGF-1 is a very important observation. In the circulation, only a very small amount of free endogenous IGF-1 is found, (<1%) and the majority of the peptide is bound to at least two different carrier proteins, a high molecular weight form, which is regulated by growth hormone and is lacking in Laron dwarfs, GHDs growth-hormone deficient dwarfs and hypophysectomized rats, and a small molecular weight form, which is in part regulated by insulin. The amount of this latter carrier protein is increased in diabetic patients. Since it has been suggested that the free IGF-1 is responsible for the insulin-like effects (e.g. hypoglycemia in vivo), it might be important to increase the free fraction of IGF-1 for the treatment of hyperglycaemia. Preliminary studies have indicated that IGF-1 would be a possible candidate to use, for example, in patients displaying insulin resistance.

Furthermore, the results from the in vivo studies on acute insulin-like activity also indicate that the O-glycosylated IGF-1 has a more pronounced effect than authentic IGF-1 in lowering the blood glucose, perhaps due to the difference in hydrophobicity of the two peptides or to a difference in kinetics.

Preliminary results of pharmacokinetics indicate that there is no difference between the O-glycosylated and the authentic IGF-1 when given to hypophysectomized rats. However, the results in normal rats indicate that the O-glycosylated form of IGF-1 may have a slightly shorter apparent half-life of the α-phase. (3.5 hours compared to 5.3 hours for the authentic IGF-1.) This might be due to a difference in binding to the carrier proteins. The computer readable form of the sequences is the same as the printed forms of the sequences SEQ ID:1 and SEQ ID:2.

We claim:

1. O-glycosylated IGF-1 essentially free from unglycosylated form of IGF-1, said O-glycosylated IGF-1 having two mannose residues attached to the Thr$_{29}$ amino acid of the IGF-1 polypeptide chain.

2. A pharmaceutical composition containing O-glycosylated IGF-1 of claim 1, but substantially no unglycosylated IGF-1 of claim 1, and a pharmaceutically acceptable carrier.

3. A pharmaceutical composition according to claim 2, also including insulin.

* * * * *